(12) United States Patent
Breiner et al.

(10) Patent No.: US 9,206,112 B2
(45) Date of Patent: Dec. 8, 2015

(54) STABILIZED (METH)ACRYLIC MONOMERS

(71) Applicants: Christine Maria Breiner, Laudenbach (DE); Klaus Dorn, Hanau (DE); Joachim Knebel, Alsbach-Haehnlein (DE); Thorben Schuetz, Alsbach-Haehnlein (DE)

(72) Inventors: Christine Maria Breiner, Laudenbach (DE); Klaus Dorn, Hanau (DE); Joachim Knebel, Alsbach-Haehnlein (DE); Thorben Schuetz, Alsbach-Haehnlein (DE)

(73) Assignee: EVONIK ROEHM GmbH, Darmstadt (DE)

( * ) Notice: Subject to any disclaimer, the term of this patent is extended or adjusted under 35 U.S.C. 154(b) by 0 days.

(21) Appl. No.: 14/383,023

(22) PCT Filed: Mar. 1, 2013

(86) PCT No.: PCT/EP2013/054159
§ 371 (c)(1),
(2) Date: Sep. 4, 2014

(87) PCT Pub. No.: WO2013/131818
PCT Pub. Date: Sep. 12, 2013

(65) Prior Publication Data
US 2015/0073171 A1    Mar. 12, 2015

(30) Foreign Application Priority Data
Mar. 5, 2012  (DE) .......................... 10 2012 203 362

(51) Int. Cl.
*C07C 69/00* (2006.01)
*C07C 67/62* (2006.01)
*C08K 5/107* (2006.01)
*C07C 69/732* (2006.01)

(52) U.S. Cl.
CPC ............... *C07C 67/62* (2013.01); *C07C 69/732* (2013.01); *C08K 5/107* (2013.01)

(58) Field of Classification Search
CPC ...... C07C 67/62; C07C 69/54; C07C 69/732; C08K 5/107
See application file for complete search history.

(56) References Cited

U.S. PATENT DOCUMENTS

| 5,322,960 A | 6/1994 | Sakamoto et al. |
| 2001/0006226 A1 | 7/2001 | Ishida et al. |
| 2004/0186311 A1 | 9/2004 | Schmitt et al. |

FOREIGN PATENT DOCUMENTS

| EP | 0 620 206 | 10/1994 |
| EP | 1 125 919 | 8/2001 |
| WO | 03 006417 | 1/2003 |

OTHER PUBLICATIONS

International Search Report issued May 22, 2013 in PCT/EP13/054159 Filed Mar. 1, 2013.

*Primary Examiner* — Yevegeny Valenrod
*Assistant Examiner* — Blaine G Doletski
(74) *Attorney, Agent, or Firm* — Oblon, McClelland, Maier & Neustadt, L.L.P.

(57) ABSTRACT

The present invention relates to the stabilization of (meth) acrylic monomers against premature polymerization during synthesis, storage and transport. The term "(meth)acrylic monomers" is understood to mean derivatives both of methacrylic acid and of acrylic acid.

13 Claims, No Drawings

STABILIZED (METH)ACRYLIC MONOMERS

The present invention relates to the stabilization of (meth) acrylic monomers against premature polymerization during synthesis, storage and transport. The term "(meth)acrylic monomers" is understood to mean derivatives both of methacrylic acid and of acrylic acid.

Due to the polymerization tendency of (meth)acrylic compounds, it is generally customary to stabilize them against premature polymerization and to add polymerization inhibitors to them during synthesis, storage and transport. The polymerization inhibitors used to date have been numerous compounds, including phenol compounds, for example hydroquinone, methylhydroquinone, tert-butylhydroquinone, 2,6-di-tert-butyl-para-hydroquinone, 2,5-di-tert-butylhydroquinone, 2,4-dimethyl-6-tert-butylphenol and hydroquinone monomethyl ether, or para-phenylenediamines, for example N-isopropyl-N'-phenyl-para-phenylenediamine, N-(1,3-dimethylbuty)-N'-phenyl-para-phenylenediamine, N-(1-methylheptyl)-N'-phenyl-para-phenylenediamine, N,N'-diphenyl-para-phenylenediamine and N,N'-di-2-naphthyl-para-phenylenediamine, or amines, for example thiodiphenylamine.

For example, EP 0522709 describes particular N,N'-dinitrosophenylenediamines for stabilization of acrylic esters. In addition, EP 0620206 claims stabilizer combinations of at least one N-oxyl compound, at least one phenol compound and at least one phenothiazine.

Further stabilizers are described in Römpp-Lexikon Chemie; editors: J. Falbe, M. Regitz; Stuttgart, New York; 10th edition (1996); under "Antioxidantien" [Antioxidants] and the references cited here.

In spite of this multitude of stabilizer solutions already available, there is still a need, for particular relatively high-reactivity (meth)acrylic monomers, for example hydroxyethyl (meth)acrylate, to achieve more efficient polymerization inhibition, or a way of doing so which causes fewer side effects, for example unwanted discolouration, during synthesis, transport and storage.

This object is achieved in the context of the present invention by stabilized (meth)acrylic monomers comprising the compound of the formula (1) as polymerization inhibitors.

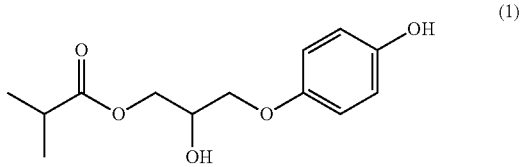 [SMILES: CC(C)C(=O)OCC(O)COc1ccc(O)cc1]

(1)

The presence of this compound as a polymerization inhibitor during synthesis, storage and transport of (meth)acrylic esters ensures sufficient stabilization without leading to discolouration. Moreover, it is incorporated into the polymer chain due to the presence of a methacrylate function in the course of polymerization in the actual use of these (meth) acrylic ester monomers for preparation of polymers, and this prevents, for example, unwanted later bleeding (the release of low molecular weight constituents) of the polymerization inhibitor.

For preparation of the compound of the formula (1), it is possible to use synthetic organic chemistry methods known to those skilled in the art. A particularly suitable method is preparation from glycidyl methacrylate and hydroquinone.

Suitable concentrations for achievement of a stabilizing effect are 0.0001 to 2% by weight, preferably 0.001 to 1.5% by weight and more preferably 0.002 to 1% by weight, based on the (meth)acrylic monomer to be stabilized, or, when mixtures of (meth)acrylic monomers are present, on the total amount of monomers present.

Monomers suitable for stabilization include (meth)acrylic esters which derive from saturated alcohols, such as hexyl (meth)acrylate, 2-ethylhexyl (meth)acrylate, heptyl (meth)acrylate, 2-(tert-butylamino)ethyl (meth)acrylate, octyl (meth)acrylate, 3-isopropylheptyl (meth)acrylate, nonyl (meth)acrylate, decyl (meth)acrylate, undecyl (meth)acrylate, 5-methylundecyl (meth)acrylate, dodecyl (meth)acrylate, 2-methyldodecyl (meth)acrylate, tridecyl (meth)acrylate, 5-methyltridecyl (meth)acrylate, tetradecyl (meth)acrylate, pentadecyl (meth)acrylate, hexadecyl (meth)acrylate, 2-methylhexadecyl (meth)acrylate, heptadecyl (meth)acrylate, 5-isopropylheptadecyl (meth)acrylate, 4-tert-butyloctadecyl (meth)acrylate, 5-ethyloctadecyl (meth)acrylate, 3-isopropyloctadecyl (meth)acrylate, octadecyl (meth)acrylate, nonadecyl (meth)acrylate, eicosyl (meth)acrylate, cetyleicosyl (meth)acrylate, stearyleicosyl (meth)acrylate, docosyl (meth)acrylate and/or eicosyltetratriacontyl (meth)acrylate; (meth)acrylates which derive from unsaturated alcohols, for example 2-propynyl (meth)acrylate, allyl (meth)acrylate, vinyl (meth)acrylate, oleyl (meth)acrylate; cycloalkyl (meth)acrylates such as cyclopentyl (meth)acrylate, 3-vinylcyclohexyl (meth)acrylate, cyclohexyl (meth)acrylate, bornyl (meth)acrylate; (meth)acrylates having two or more (meth)acryloyl groups, glycol di(meth)acrylates such as ethylene glycol di(meth)acrylate, diethylene glycol di(meth)acrylate, triethylene glycol di(meth)acrylate, tetra- and polyethylene glycol di(meth)acrylate, 1,3-butanediol (meth)acrylate, 1,4-butanediol (meth)acrylate, 1,6-hexanediol di(meth)acrylate, glyceryl di(meth)acrylate and dimethacrylates of ethoxylated bisphenol A; (meth)acrylates having three or more double bonds, for example glyceryl tri(meth)acrylate, trimethylolpropane tri(meth)acrylate, pentaerythrityl tetra(meth)acrylate and dipentaerythrityl penta (meth)acrylate. These additionally include (meth)acrylates which derive from polymers having at least one hydroxyl group, for example polyalkylene glycol mono(meth)acrylates and polyalkylene glycol di(meth)acrylates. The preferred (meth)acrylic esters likewise include polyalkylene glycol mono(meth)acrylates, especially polyethylene glycol mono(meth)acrylates, polypropylene glycol mono(meth) acrylates and polybutylene glycol mono(meth)acrylates, and polyalkylene glycol di(meth)acrylates, especially polyethylene glycol di(meth)acrylates, polypropylene glycol di(meth) acrylates and polybutylene glycol di(meth)acrylates.

Also suitable for inventive stabilization are hydroxyalkyl (meth)acrylates. Preferred hydroxyalkyl (meth)acrylates include 2-hydroxyethyl (meth)acrylate, 2-hydroxypropyl (meth)acrylate, 3-hydroxypropyl (meth)acrylate and 3,4-dihydroxybutyl (meth)acrylate. Compounds of particular interest are those selected from the group consisting of hydroxyethyl acrylate (HEA), hydroxyethyl methacrylate (HEMA), 2-hydroxypropyl acrylate (2-HPA), 2-hydroxypropyl methacrylate (2-HPMA), 3-hydroxypropyl acrylate (3-HPA), 3-hydroxypropyl methacrylate (3-HPMA), 2,3-dihydroxypropyl acrylate, 2,3-dihydroxypropyl methacrylate, 1,3-diacryloylglycerol, 1,3-dimethacryloylglycerol, trimethylolpropane monoacrylate, trimethylolpropane monomethacrylate, trimethylolpropane diacrylate and trimethylolpropane dimethacrylate.

The ethylenically unsaturated monomers may be present individually or as a mixture in the inventive composition.

Also suitable for stabilization are (meth)acrylamides of the formula (2)

$$CH_2=CR^3-CO-NHR^2 \quad (2)$$

where $R^3$ is hydrogen or the methyl group. $R^2$ is a linear, branched or cyclic alkyl radical, an aryl radical which may also be substituted by one or more alkyl groups. The linear, cyclic or branched alkyl radical may have a length of 1 to 12 carbon atoms and may, for example, be methyl, ethyl, propyl, isopropyl, butyl, isobutyl, tert-butyl, pentyl, hexyl, heptyl, octyl, isooctyl, nonyl, decyl, undecyl, and may optionally be mono- or polysubstituted by $-NR^3R^4$ or $-OR^5$, where either $R^3$ or $R^4$ may adopt the definition of hydrogen and where, in addition: $R^3$, $R^4$ or $R^6$ may either be the same or different and are each an alkyl group having 1 to 12 carbon atoms, for example methyl, ethyl, propyl, isopropyl, butyl, isobutyl, tert-butyl, pentyl, hexyl, heptyl, octyl, isooctyl, nonyl, decyl, undecyl or hydrogen. $R^2$ may additionally also be $[(R^6-O)_n]-R^7$ where: n may assume the values of 1 to 4; $-R^6$ may be a C1-C4-alkyl group which may also be branched, for example methyl, ethyl, propyl, isopropyl, butyl, isobutyl or tert-butyl; $R^7$ may be the methyl group or the ethyl group.

(Meth)acrylate derivatives particularly suitable for stabilization are those based on polyunsaturated fatty acid components as described, for example, in EP 2217629, EP 2283075, EP2334634, DE 102009001964 and DE102009001965. The content of these publications is hereby considered to be disclosed. These are essentially (meth)acrylic monomers of the formula (3)

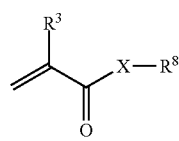

(3)

in which the $R^3$ radical is hydrogen or methyl and —X— is independently

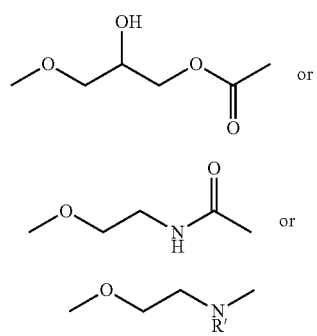

(4)

(5)

(6)

in which R' is hydrogen or a radical having 1 to 6 carbon atoms, and $R^8$ is a linear or branched radical which has 8 to 40, preferably 10 to 30 and more preferably 12 to 20 carbon atoms and which has at least one C—C double bond.

The examples which follow are intended to illustrate but in no way to restrict the invention.

EXAMPLE 1

Synthesis of the Glycidyl Methacrylate-Hydroquinone Adduct (Formula (1))

A mixture of 9.95 g of glycidyl methacrylate, 4.40 g of hydroquinone, 0.050 g of HEPTCR 050 NPG (chromium heptanoate in polypropylene glycol) and 50 ml of o-xylene is initially charged in a 250 ml four-neck flask with a sabre stirrer (stirrer sleeve, stirrer motor), a thermometer, an inlet tube for compressed air, a reflux condenser and an oil bath with temperature regulation. The reaction mixture was heated to boiling with introduction of air. This was followed by refluxing at a reaction temperature (=internal flask temperature) of 142° C. for 10 h. After cooling to room temperature, the volatile constituents were removed in a rotary evaporator (bath temperature 55° C., vacuum 20 mbara). After filtration, a brown, cloudy liquid was obtained. The synthesis product was purified by means of column and thin-layer chromatography. The stationary phase used for column chromatography was silica gel 60 (0.063-0.200 mm); the eluent consisted of an ethyl acetate/cyclohexane mixture in a ratio of 1/1. The clear and colourless solutions obtained were combined to give three fractions. The eluent was subsequently removed on a rotary evaporator.

EXAMPLE 2

The inventive compound prepared in Example 1 was introduced into UHP HEMA (ultra high purity hydroxyethyl methacrylate, commercially available as Visiomer® UHP HEMA, from Evonik Industries AG, Germany) and the polymerization time thereof was determined, as was discolouration via colour number. The results are shown in Tab. 1.

COMPARATIVE EXAMPLE

As a comparative inhibitor, N,N-diphenylenediamine was introduced into ultra high purity hydroxyethyl methacrylate and polymerization time and discolouration via colour number were determined. The results are likewise shown in Tab. 1.

TABLE 1

Polymerization times and colour numbers

| Concentration/ ppm | Example 2 | | Comparative example | |
|---|---|---|---|---|
| | Polymerization time/min | Colour number Pt/Co | Polymerization time/min | Colour number Pt/Co |
| 0 | 70.7 | 8 | 71.2 | 8 |
| 5 | 70.5 | 12 | 102.7 | 59 |
| 20 | 75.0 | 18 | 183.3 | 193 |
| 50 | 81.3 | 28 | 325.8 | 400 |
| 100 | 94.8 | 35 | 589.2 | 676 |

It becomes clearly evident from Tab. 1 that the inventive inhibitor has much better colour values with adequate inhibitor performance.

Method for Determination of Polymerization Time

The polymerization time is defined as the time that a mixture, from the commencement of polymerization, needs to attain the polymerization peak temperature with addition of an initiator. In the present examples, 0.1% AIBN was used at a polymerization temperature of 55° C. The result reported is the time needed. The measurement is effected by means of a contact thermometer and recording of the temperature variation.

Method for Determination of Colour Number

The colour number was determined by means of the process explained in detail in DE 10131479 (determination of colour by the platinum-cobalt scale; also called APHA or turbidity number). This process was developed based on DIN EN ISO 6271.

The invention claimed is:

1. A composition comprising a (meth)acrylic monomer and a compound of formula (1)

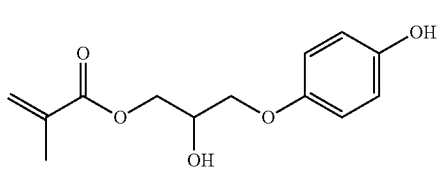

as a polymerization inhibitor.

2. The composition of claim 1, wherein a concentration of the compound of formula (1) is from 0.0001 to 2% by weight, based on the (meth)acrylic monomer.

3. The composition of claim 1, wherein the (meth)acrylic monomer is hydroxyethyl methacrylate.

4. The composition of claim 1, wherein the (meth)acrylic monomer is of formula (3)

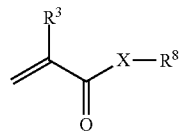

wherein the $R^3$ radical is hydrogen or methyl and —X— is independently

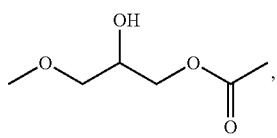

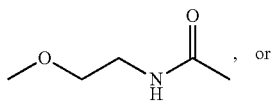

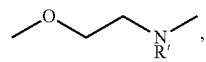

wherein R' is hydrogen or a radical having 1 to 6 carbon atoms, and $R^8$ is a linear or branched radical which has 8 to 40 carbon atoms and which has a C—C double bond.

5. The composition of claim 2, wherein the concentration of the compound of formula (1) is from 0.001 to 1.5% by weight.

6. The composition of claim 2, wherein the concentration of the compound of formula (1) is from 0.002 to 1% by weight.

7. The composition of claim 4, wherein $R^8$ is a linear radical.

8. The composition of claim 4, wherein $R^8$ is a branched radical.

9. The composition of claim 4, wherein $R^8$ is a linear or branched radical which has 10 to 30 carbon atoms.

10. The composition of claim 4, wherein $R^8$ is a linear or branched radical which has 12 to 20 carbon atoms.

11. The composition of claim 4, wherein —X— is

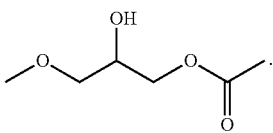

12. The composition of claim 4, wherein —X— is

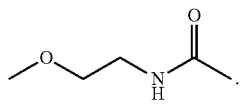

13. The composition of claim 4, wherein —X— is

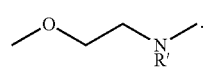

* * * * *